(12) United States Patent
Furo et al.

(10) Patent No.: US 11,395,800 B2
(45) Date of Patent: Jul. 26, 2022

(54) PHARMACEUTICAL TABLET AND PRODUCTION METHOD THEREOF

(71) Applicant: Mitsubishi Chemical Corporation, Tokyo (JP)

(72) Inventors: Chizuko Furo, Tokyo (JP); Ayaka Kobayashi, Tokyo (JP); Hirofumi Takeuchi, Gifu (JP); Yoshiko Takeuchi, Gifu (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/784,692

(22) Filed: Feb. 7, 2020

(65) Prior Publication Data

US 2020/0170955 A1 Jun. 4, 2020

Related U.S. Application Data

(63) Continuation of application No. PCT/JP2018/029823, filed on Aug. 8, 2018.

(30) Foreign Application Priority Data

Aug. 8, 2017 (JP) .............................. JP2017-153172

(51) Int. Cl.
*A61K 9/20* (2006.01)

(52) U.S. Cl.
CPC .......... *A61K 9/2027* (2013.01); *A61K 9/2013* (2013.01); *A61K 9/2095* (2013.01)

(58) Field of Classification Search
CPC .. A61K 9/2027; A61K 9/2013; A61K 9/2095; A61K 9/20; A61K 47/32; A61K 47/12; A61K 47/10
See application file for complete search history.

(56) References Cited

U.S. PATENT DOCUMENTS

| | | | | |
|---|---|---|---|---|
| 2012/0041118 A1* | 2/2012 | Shibutani | .................. | C08J 5/18 524/284 |
| 2012/0087986 A1* | 4/2012 | Nagesh | .................. | A61P 25/24 424/497 |
| 2017/0209377 A1* | 7/2017 | Furo | ......................... | C08J 3/12 |
| 2020/0087465 A1* | 3/2020 | Fukamachi | ............ | C08K 5/053 |

FOREIGN PATENT DOCUMENTS

| | | |
|---|---|---|
| EP | 2400954 A2 | 1/2012 |
| JP | 2013-087074 | 5/2013 |
| JP | 2016-102101 | 6/2016 |
| WO | 2006-029787 A1 | 3/2006 |
| WO | 2010-097243 A2 | 9/2010 |
| WO | 2016/161069 | 10/2016 |

OTHER PUBLICATIONS

Kitamura, S. et al., "Review on utilization of PVA particles, to which platicizer is added, as direct compression-binding agent", Formulation seminar of the Academy of Pharmaceutical Science and Technology, Aug. 1, 2017, pp. 71, with English translation thereof.
Mohsin, M et al., "Thermal and Mechanical Properties of Poly(vinyl alcohol) Plasticized with Glycerol", Journal of Applied Polymer Science, vol. 122, issue. 5, 2011, pp. 3102-3109.
International Search Report issued in International Patent Application No. PCT/JP2018/029823, dated Oct. 23, 2018 with English translation.
Written Opinion of the International Searching Authority issued in International Application No. PCT/JP2018/029823, dated Oct. 16, 2018 with English translation.
International Preliminary Report on Patentability issued in International Patent Application No. PCT/JP2018/029823, dated Feb. 11, 2020 with English translation.
Extended European Search Report, European Patent Office, Application No. 18843910.3 dated Jul. 7, 2020.
Eva Snejdrova et al: "Pharmaceutical Applications of Plasticized Polymers" In: "Recent Advances in Plasticizers", Mar. 21, 2012 (Mar. 21, 2012).
Volker Bühler: "Pharmaceutical . . . Services.", Jun. 1, 2008 (Jun. 1, 2008), URL:http://www.pharma-ingredients.basf.com/documents/komplett_pharmaceutical_technology_.pdf.
European Office Action, EPO, Application No. 18843910.3, dated Mar. 16, 2021.
Indian Office Action, India Patent Application No. 202017005468, dated Dec. 27, 2020, English translation.
Hearing Notice, Intellectual Property India, Application No. 202017005468, issued May 10, 2021.
Japanese Office Action Japanese Patent Application No. 2018-542307, dated Apr. 12, 2022, English translation.

* cited by examiner

*Primary Examiner* — Snigdha Maewall
(74) *Attorney, Agent, or Firm* — Greenblum & Bernstein, P.L.C.

(57) ABSTRACT

An object of the present invention is to provide a pharmaceutical tablet having high tensile strength and excellent in immediate disintegrability. The pharmaceutical tablet of the present invention is obtained by a direct compression method, and contains an active ingredient, a polyvinyl alcohol resin, and a plasticizer other than water, wherein a content of the plasticizer is 1 to 8 parts by weight with respect to 100 parts by weight of the polyvinyl alcohol resin.

5 Claims, No Drawings

PHARMACEUTICAL TABLET AND PRODUCTION METHOD THEREOF

CLAIM FOR PRIORITY

This application is a Continuation of PCT/JP2018/029823 filed Aug. 8, 2018, and claims the priority benefit of Japanese application 2017-153172 filed Aug. 8, 2017, the contents of which are expressly incorporated by reference herein in their entireties.

TECHNICAL FIELD

The present invention relates to a pharmaceutical tablet which contains a polyvinyl alcohol resin and which is tableted and molded by a direct compression method, and a method for producing the pharmaceutical tablet.

BACKGROUND ART

Currently, oral preparations such as tablets, capsules, granules, and powders are most widely used as pharmaceutical dosage forms. The tablet which is one of them is generally produced by tablet-forming. With respect to the method of tablet-forming, a granule obtained by granulating a powder mixture obtained by mixing various additive components with an effective ingredient (active ingredient) as a medicament is charged into a die, or the powder mixture is charged directly into a die, and molded into the desired size and shape by being compressed with punch, so as to obtain the pharmaceutical tablet. The molded tablets may be coated as required.

In addition to the effective ingredient, examples of the additive components include binders, excipients, disintegrants, and lubricants. Among these additive components, the binder is added to bind powder particles of raw materials and has large impact on the mechanical strength of the tablet. When the binder is not appropriately selected, there are problems such as molding failure, and tablet breaking after molding. The binder also affects the dissolution rate of the active ingredient since the active ingredient is not easily absorbed if the tablet does not disintegrate when entering body.

Therefore, a binder to be used for a pharmaceutical tablet is required to satisfy both mechanical strength during storage of the pharmaceutical tablet and dissolution control when the pharmaceutical tablet is taken.

In recent years, the direct compression method has attracted attention as a method for producing the pharmaceutical tablet. The direct compression method is a method of producing the tablet by mixing an active ingredient (medicinal ingredient), a binder, an excipient, a lubricant and other components in solid forms, and compressing the resulting mixture directly with a tableting machine without performing a granulation step. Therefore, the direct compression method has a great advantage from the viewpoint of commercial production since the manufacturing process can be shortened and the manufacturing efficiency is good, and also has an advantage of being applicable to an active ingredient (active ingredient) unstable to moisture since tableting can be performed without using moisture necessary for the granulation step.

As a binder to be used in the direct compression method, for example, Patent Literature 1 discloses a pharmaceutical binder containing a polyvinyl alcohol (co)polymer.

CITATION LIST

Patent Literature

Patent Literature 1: JP-A-2013-87074

SUMMARY OF INVENTION

Technical Problem

However, a tablet produced by directly tableting a mixture containing a binder and an active ingredient described in Patent Literature 1 has not yet been satisfactory in mechanical strength.

Therefore, under such circumstances, an object of the present invention is to provide a pharmaceutical tablet having high tensile strength and excellent in immediate disintegrability, and to provide a method for producing the pharmaceutical tablet.

Solution to Problem

The present inventors have conducted intensive studies to find a solution to the foregoing problems, and found that the problems can be solved by using a polyvinyl alcohol resin as a binder, containing a combination of a polyvinyl alcohol resin and a plasticizer other than water, and tableting and molding, by a direct compression method, a powder mixture obtained by mixing the above components. The present invention was completed on the basis of this finding.

That is, the gist of the present invention relates to a pharmaceutical tablet obtained by a direct compression method, and the pharmaceutical tablet contains an active ingredient, a polyvinyl alcohol resin, and a plasticizer other than water, wherein a content of the plasticizer is 1 to 8 parts by weight with respect to 100 parts by weight of the polyvinyl alcohol resin.

In the pharmaceutical tablet of the present invention, an average degree of polymerization of the polyvinyl alcohol resin is preferably 2100 to 4000, tensile strength of the pharmaceutical tablet is preferably 1.0 MPa or more, and a degree of saponification of the polyvinyl alcohol resin is preferably 70 mol % to 100 mol %.

In addition, in the pharmaceutical tablet of the present invention, the plasticizer is preferably a liquid polyhydric alcohol at 25° C., and is preferably substantially free of water.

In addition, the gist of the present invention relates to a method for producing a pharmaceutical tablet, the method including: tableting and molding, by a direct compression method, a powder mixture containing an active ingredient and a polyvinyl alcohol resin impregnated with a plasticizer other than water.

Advantageous Effects of Invention

Since the pharmaceutical tablet of the present invention has high tensile strength, it is difficult to break during molding or transportation, and since the pharmaceutical tablet of the present invention is excellent in immediate disintegrability, dissolution control is easy when being taken. According to the production method of the present invention, the pharmaceutical tablet of the present invention can also be easily produced.

DESCRIPTION OF EMBODIMENTS

The description of the constituent requirements described below is an example (representative example) of an embodiment of the present invention, and the present invention is not limited to these contents.

In the present description, the term "(co)polymer" means a polymer or a copolymer, the term "(meth)allyl" means allyl or methallyl, the term "(meth)acryl" means acryl or methacryl, and the term "(meth)acrylate" means acrylate or methacrylate.

A pharmaceutical tablet of the present embodiment contains at least an active ingredient, a polyvinyl alcohol resin, and a plasticizer other than water. Hereinafter, the polyvinyl alcohol resin, the plasticizer, and the active ingredient will be described in this order.

[Polyvinyl Alcohol Resin]

In the present embodiment, the polyvinyl alcohol (hereinafter, referred to as PVA) resin is used as a binder, and the PVA resin used in the present embodiment includes an unmodified PVA and/or a modified PVA.

Examples of the modified PVA include a copolymer-modified PVA and a post-modified PVA. The modification amount varies depending on the property of a modifying group, and is generally 1 mol % to 20 mol %, preferably 1 mol % to 10 mol %, and particularly preferably 1 mol % to 5 mol %.

The above copolymer-modified PVA can be produced by copolymerizing a vinyl ester monomer such as vinyl acetate, and another unsaturated monomer copolymerizable with the vinyl ester monomer and then saponifying the copolymer.

The unmodified PVA can generally be produced by saponifying a polymer obtained by polymerizing a vinyl ester monomer such as vinyl acetate.

The (co)polymerization of the vinyl ester monomer for the unmodified PVA or the copolymer-modified PVA can be performed by any known polymerization method such as solution polymerization, suspension polymerization, and emulsion polymerization. Among these, it is preferable to perform the solution polymerization which can efficiently remove the reaction heat under reflux. As a solvent for the solution polymerization, an alcohol is generally used, and a lower alcohol having 1 to 3 carbon atoms is preferably used.

For the saponification of the obtained (co)polymer, a known saponification method in the related can be employed. That is, the saponification can be performed using an alkali catalyst or an acid catalyst in a state where the polymer is dissolved in an alcohol or a water/alcohol solvent.

As the alkali catalyst, for example, alkali metal hydroxides such as potassium hydroxide, sodium hydroxide, sodium methylate, sodium ethylate, potassium methylate, and lithium methylate, or alcoholate can be used.

Generally, saponification is preferably performed by a transesterification reaction using an alkali catalyst in the presence of an anhydrous alcohol solvent in terms of reaction rate or reduction of impurities such as fatty acid salts.

The reaction temperature of the saponification reaction is generally 20° C. to 60° C. When the reaction temperature is excessively low, the reaction rate tends to decrease and the reaction efficiency tends to decrease; when the reaction temperature is excessively high, the boiling point of the reaction solvent may be exceeded, and the safety in production tends to decrease. In a case of performing the saponification under a high pressure using a tower-type continuous saponification tower with high pressure resistance, the saponification can be performed at a higher temperature, for example, 80° C. to 150° C., and a PVA resin with a high degree of saponification can be obtained in a short time by using a small amount of saponification catalyst.

After saponification, the obtained PVA resin is preferably washed with a washing liquid.

Examples of the washing liquid include alcohols such as methanol, ethanol, isopropyl alcohol, and butanol. Preferred for washing efficiency and drying efficiency is methanol.

The washing may be performed continuously. However, batch washing is generally employed. The bath ratio (weight of washing liquid to weight of PVA resin) is generally 1 to 30, particularly preferably 2 to 20. When the bath ratio is excessively large, a large washing device will be required, and the cost tends to increases; when the bath ratio is excessively small, washing performance tends to be poor, and the washing tends to be performed frequently.

The washing temperature is generally 10° C. to 80° C., particularly preferably 20° C. to 70° C. When the washing temperature is excessively high, the vaporization amount of the washing liquid increases, and reflux equipment tends to be necessary. When the washing temperature is excessively low, the washing efficiency tends to decrease. The washing time is generally 5 minutes to 12 hours. When the washing time is excessively long, the production efficiency tends to decrease; when the washing time is excessively short, the washing tends to be insufficient. The washing is performed generally 1 to 10 times, particularly preferably 1 to 5 times. When washing is performed too frequently, productivity becomes poor and the cost tends to increase.

The washed PVA resin is dried with, for example, hot air, either continuously or in a batch. The drying temperature (temperature in a dryer) is generally 50° C. to 150° C. When the drying temperature is excessively high, the PVA resin tends to be thermally deteriorated; when the drying temperature is excessively low, it tends to take a long time for drying. The drying time is generally 1 to 48 hours. When the drying time is excessively long, the PVA resin tends to be thermally deteriorated; when the drying time is excessively short, the drying tends to be insufficient or high temperature drying tends to be required.

The content of the solvent in the PVA resin after drying is generally 0 wt % to 10 wt %, preferably 0.1 wt % to 5 wt %, and more preferably 0.1 wt % to 1 wt %.

The PVA resin generally contains an alkali metal salt of acetic acid derived from an alkali catalyst used during the saponification. The content of the alkali metal salt of acetic acid is generally 0.001 wt % to 2 wt %, preferably 0.005 wt % to 1 wt %, and more preferably 0.01 wt % to 0.1 wt % with respect to the PVA resin.

When the content of the alkali metal salt is excessively large, the stability of the active ingredient tends to decrease. Examples of a method of adjusting the content of the alkali metal salt include a method of adjusting the amount of the alkali catalyst used for saponification, or a method of washing the PVA resin with alcohols such as ethanol and methanol in the washing step.

In the present embodiment, the alkali metal salt may be quantified by, for example, dissolving the PVA resin powder in water, and determining the content of the alkali metal salt through neutralization titration with hydrochloric acid, using methyl orange as an indicator.

Examples of the other unsaturated monomer copolymerizable with the vinyl ester monomer include: olefins such as ethylene, propylene, isobutylene, α-octene, α-dodecene, and α-octadecene; unsaturated acids such as an acrylic acid, a methacrylic acid, a crotonic acid, a maleic acid, a maleic anhydride, an itaconic acid, and an undecylenic acid, or a salt thereof, a mono- or di-alkyl ester thereof; nitriles such as acrylonitrile and methacrylonitrile; amides such as diacetone acrylamide, acrylamide and methacrylamide; olefin sulfonic acids such as an ethylene sulfonic acid, an allyl sulfonic acid, and a methallyl sulfonic acid or a salt thereof; alkyl vinyl ethers; N-acrylamidomethyltrimethylammonium chloride; allyltrimethylammonium chloride; dimethylallyl vinyl ketone; N-vinyl pyrrolidone; vinyl chloride; vinylidene chloride; polyoxyalkylene (meth)allyl ethers such as polyoxyethylene (meth)allyl ether and polyoxypropylene (meth)allyl ether; polyoxyalkylene (meth)acrylates such as polyoxyethylene (meth)acrylate and polyoxypropylene (meth)acrylate; polyoxyalkylene (meth)acrylamides such as polyoxyethylene (meth)acrylamide and polyoxypropylene (meth)acrylamide; polyoxyethylene (1-(meth)acrylamide-1,1-dimethylpropyl) ester; polyoxyalkylene vinyl ethers such as polyoxyethylene vinyl ether and polyoxypropylene vinyl ether; polyoxyalkylene allylamines such as polyoxyethylene allylamine and polyoxypropylene allylamine; polyoxyalkylene vinylamines such as polyoxyethylene vinylamine and polyoxypropylene vinylamine; hydroxy group-containing α-olefins such as 3-buten-1-ol, 4-penten-1-ol, and 5-hexen-1-ol, or an acylated product thereof; vinyl ethylene carbonate; 2,2-dialkyl-4-vinyl-1,3-dioxolane; a glycerin monoallyl ether; vinyl compounds such as 3,4-diacetoxy-1-butene; isopropenyl acetate; substituted vinyl acetates such as 1-methoxyvinyl acetate; 1,4-diacetoxy-2-butene; and vinylene carbonate.

Examples of the copolymer-modified PVA include a PVA resin having a primary hydroxyl group in the side chain. Examples of such a PVA resin include: a PVA resin having a 1,2-diol bond in the side chain, obtained by copolymerization of 3,4-diacetoxy-1-butene, vinylethylene carbonate, and glycerin monoallyl ether; and a PVA resin having a hydroxymethyl group in the side chain, obtained by copolymerization of hydroxymethylvinylidene diacetates such as 1,3-diacetoxy-2-methylenepropane, 1,3-dipropionyloxy-2-methylenepropane, and 1,3-dibutyronyloxy-2-methylenepropane.

The PVA resin having a 1,2-diol bond in the side chain is obtained by, for example, (a) a method of saponifying a copolymer of a vinyl ester monomer and 3,4-diacetoxy-1-butene, (b) a method of saponifying and decarboxylating a copolymer of a vinyl ester monomer and vinyl ethylene carbonate, (c) a method of saponifying and deketalizing a copolymer of a vinyl ester monomer and 2,2-dialkyl-4-vinyl-1,3-dioxolane, and (d) a method of saponifying a copolymer of a vinyl ester monomer and a glycerin monoallyl ether.

The post-modified PVA can be produced by post-modifying an unmodified PVA. Examples of the post-modification method include a method of subjecting an unmodified PVA to acetic esterification, acetalization, urethanization, etherification, phosphate esterification or oxyalkylene formation.

In the present embodiment, it is preferable to use an unmodified PVA resin as the PVA resin.

As the PVA resin, among the various PVA resins described above, one type can be used alone, or two or more types can be mixed and used in combination.

The average degree of saponification (measured according to JIS K6726) of the PVA resin is generally 70 mol % to 100 mol %, preferably 78 mol % to 95 mol %, and particularly preferably 85 mol % to 90 mol %. When the average degree of saponification is excessively low, the water solubility tends to decrease.

The average degree of polymerization (measured according to JIS K6726) of the PVA resin is generally 200 to 4000, preferably 500 to 4000, more preferably 1000 to 4000, still more preferably 2100 to 4000, particularly preferably 2100 to 3800, and most preferably 2200 to 3500. When the average degree of polymerization is excessively low, the mechanical strength of the pharmaceutical tablet tends to decrease; when the average degree of polymerization is excessively high, the immediate disintegrability of the pharmaceutical tablet tends to decrease.

Examples of the form of the PVA resin generally include powder or granule form, and the powder or granule form is preferred. The average particle size of the PVA resin is generally 1 μm to 200 μm, preferably 5 μm to 170 μm, and particularly preferably 10 μm to 150 μm. When the average particle size is excessively small, handling tends to be difficult due to scattering; when the average particle size is excessively large, the strength of the tablet tends to decrease.

The average particle size of the PVA resin in the present embodiment is a 50% particle size, which is the diameter at 50% in the cumulative value (cumulative distribution) obtained from the measured laser diffraction volume distribution by particle size.

The pharmaceutical tablet of the present embodiment may contain a binder other than the PVA resin, and examples of such a binder include hydroxypropylcellulose, starch paste, and gum arabic paste.

In the case of using a binder other than the PVA resin, the content of the PVA resin in the binder is preferably 50 wt % or more, particularly preferably 80 wt % or more, and further preferably 90 wt % or more. When the content of the PVA resin is excessively small, the effect of the present invention tends to be difficult to obtain.

The content of the binder is generally 0.1 wt % to 80 wt %, preferably 0.5 wt % to 50 wt %, and particularly preferably 1 wt % to 10 wt % in the pharmaceutical tablet. When the content of the binder is excessively small, the strength of the tablet tends to be insufficient; when the content of the binder is excessively large, the dissolution rate of the active ingredient tends to decrease.

[Plasticizer]

The plasticizer used in the present embodiment is a plasticizer other than water, and is a plasticizer that can be used in pharmaceutical products. Examples of such a plasticizer include: liquid polyhydric alcohols at room temperature (25° C.) such as glycerin, ethylene glycol, diethylene glycol, triethylene glycol, propylene glycol, and polyethylene glycol having a molecular weight of about 500 to 1000; solid polyhydric alcohol at room temperature (25° C.) such as trimethylolpropane (solid) and polyethylene glycol having a molecular weight of 1500 or more; and carboxylic acid esters such as triethyl citrate. Among these, the plasticizer is preferably a liquid polyhydric alcohol at room temperature, and particularly preferably glycerin, from the viewpoint of easily obtaining the effects of the present invention.

These plasticizers can be used alone or in combination of two or more thereof.

In the present embodiment, it is preferable to impregnate the PVA resin with a plasticizer. Therefore, the plasticizer used in the present embodiment is preferably liquid at 25° C., that is, has a melting point of 25° C. or lower and a boiling point higher than 25° C. A plasticizer that is not liquid at 25° C. but can be dissolved at a concentration of 50 wt % or more at 25° C. using water or a lower alcohol having 1 to 3 carbon atoms as a solvent can also be contained as the plasticizer used in the present embodiment.

The method for impregnating the PVA resin with the plasticizer is not particularly limited, and examples thereof include a method of gradually adding and mixing a plasticizer to a PVA resin or a method of adding and mixing a PVA resin to a plasticizer solution.

The content of the plasticizer in the pharmaceutical tablet of the present embodiment is 1 to 8 parts by weight, preferably 2 to 7 parts by weight, and particularly preferably 3 to 6 parts by weight with respect to 100 parts by weight of the PVA resin. When the content of the plasticizer is excessively small, the strength of the tablet tends to be insufficient; when the content of the plasticizer is excessively large, the dissolution rate of the active ingredient tends to decrease.

[Active Ingredient]

The active ingredient contained in the pharmaceutical tablet of the present embodiment is a medicinal component exhibiting physiological activity and a nutritional component in foods and health foods. The active ingredient includes not only active ingredients alone but also active ingredients that have been coated or granulated for the purpose of sustained release or bitterness masking.

Examples of the active ingredients used in the present invention include antipyretic analgesic antiphlogistics, nutrient and tonic supplements, psychotropics, antidepressants, antianxiety drugs, hypnosedatives, anticonvulsants, CNS-acting drugs, brain metabolism improving agents, brain circulation improving agents, antiepileptic agents, sympathomimetic drugs, gastrointestinal drugs, acid suppressants, anti-ulcerogenic drugs, cough medicines, antiemetics, anapnoics, bronchodilators, allergic drugs, antihistamine agents, agents for dental and oral use, cardiants, agents for cardiac arrhythmia, diuretics, hypertension drugs, vasoconstrictors, coronary vasodilators, peripheral vasodilators, blood coagulation inhibitors, hyperlipidemias agents, cholagogues, antibiotics, chemotherapeutic agents, diabetes drugs, osteoporosis drugs, skeletal muscle relaxants, antispasmodics, antirheumatics, hormonal agents, alkaloid drugs, sulfa drugs, arthrifuges, and antineoplastics.

Examples of the antipyretic analgesic antiphlogistics include acetaminophen, aspirin, ibuprofen, ethenzamide, diphenhydramine hydrochloride, dl-chlorpheniramine maleate, diclofenac sodium, dihydrocodeine phosphate, salicylamide, aminopyrine, noscapine, methylephedrine hydrochloride, phenylpropanolamine hydrochloride, serrapeptase, lysozyme chloride, tolfenamic acid, mefenamic acid, flufenamic acid, ketoprofen, indometacin, bucolome, pentazocine, caffeine, and anhydrous caffeine.

Examples of the nutrient and tonic supplements include vitamins such as vitamin A, vitamin B1 (e.g., dibenzoylthiamine, and fursulthiamine hydrochloride), vitamin B2 (e.g., riboflavin butyrate), vitamin B6 (e.g., pyridoxine hydrochloride), vitamin B12 (e.g., hydroxocobalamin acetate, and cyanocobalamin), vitamin C (e.g., ascorbic acid, and sodium L-ascorbate), vitamin D, and vitamin E (e.g., d-α-tocopherol acetate); minerals such as calcium, magnesium, and iron; proteins, amino acids, oligosaccharides, and crude drugs.

Examples of the psychotropics include chlorpromazine, and reserpine.

Examples of the antidepressants include amphetamine, imipramine, and maprotiline hydrochloride.

Examples of the antianxiety drugs include diazepam, alprazolam, and chlordiazepoxide.

Examples of the hypnosedatives include estazolam, diazepam, nitrazepam, perlapine, and phenobarbital sodium.

Examples of the anticonvulsants include scopolamine hydrobromide, diphenhydramine hydrochloride, and papaverine hydrochloride.

Examples of the CNS-acting drugs include citicoline.

Examples of the brain metabolism improving agents include meclofenoxate hydrochloride.

Examples of the brain circulation improving agents include vinpocetine.

Examples of the antiepileptic agents include phenitoin, and carbamazepine.

Examples of the sympathomimetic drugs include isoproterenol hydrochloride.

Examples of the gastrointestinal drugs include: stomach digestive aids such as diastase, saccharated pepsin, a scopolia extract, cellulase AP3, lipase AP, and cinnamon oil; and antiflatulents such as berberine chloride, resistant lactic acid bacteria, and bifidobacteria.

Examples of the acid suppressants include magnesium carbonate, sodium bicarbonate, magnesium aluminometasilicate, synthetic hydrotalcite, precipitated calcium carbonate, and magnesium oxide.

Examples of the anti-ulcerogenic drugs include lansoprazole, omeprazole, rabeprazole, cimetidine, famotidine, and ranitidine hydrochloride.

Examples of the cough medicines include cloperastine hydrochloride, dextromethorphan hydrobromide, theophylline, guaiacol potassium sulfonate, gualfenesin, and codeine phosphate.

Examples of the antiemetics include difenidol hydrochloride, and metoclopramide.

Examples of the anapnoics include levallorphan tartrate.

Examples of the bronchodilators include theophylline, and sulbutamol sulfate.

Examples of the allergic drugs include amlexanox, and seratrodast.

Examples of the antihistamine agents include diphenhydramine hydrochloride, promethazine, isothipendyl hydrochloride, and dl-chlorpheniramine maleate.

Examples of the agents for dental and oral use include oxytetracycline, triamcinolone acetonide, chlorhexidine hydrochloride, and lidocaine.

Examples of the cardiants include digoxin, and caffeine.

Examples of the agents for cardiac arrhythmia include procainamide hydrochloride, propranolol hydrochloride, and pindolol.

Examples of the diuretics include furosemide, isosorbide, and hydrochlorothiazide.

Examples of the hypertension drugs include captopril, delapril hydrochloride, hydralazine hydrochloride, labetalol hydrochloride, manidipine hydrochloride, candesartan cilexetil, methyldopa, and perindopril erbumine.

Examples of the vasoconstrictors include phenylephrine hydrochloride.

Examples of the coronary vasodilators include carbocromen hydrochloride, molsidomine, and verapamil hydrochloride.

Examples of the peripheral vasodilators include cinnarizine.

Examples of the blood coagulation inhibitors include dicumarol.

Examples of the hyperlipidemias agents include cerivastatin sodium, simvastatin, pravastatin sodium, and an atorvastatin calcium hydrate.

Examples of the cholagogues include dehydrocholic acid, and trepibutone.

Examples of the antibiotics include various antibiotics including: cephem antibiotics such as cephalexin, cefaclor, cefotiam hexetil hydrochloride, cephadroxil, cefixime, cefditoren pivoxil, cefteram pivoxil, and cefpodoxime proxetil; penicillin antibiotics such as ampicillin, amoxicillin, cyclacillin and pipmesilinum hydrochloride; quinolone antibiotics such as nalidixic acid and enoxacin; monobactam antibiotics such as carmonam sodium; penem antibiotics; and carbapenem antibiotics.

Examples of the chemotherapeutic agents include sulfamethizole.

Examples of the diabetes drugs include glymidine sodium, glipizide, phenformin hydrochloride, buformin hydrochloride, metformin, metformin hydrochloride, tolbutamide, voglibose, pioglitazone hydrochloride, glibenclamide, and troglitazone.

Examples of the osteoporosis drugs include ipriflavone.

Examples of the skeletal muscle relaxants include methocarbamol.

Examples of the antispasmodics include meclizine hydrochloride, and dimenhydrinate.

Examples of the antirheumatics include methotrexate, and bucillamine.

Examples of the hormonal agents include liothyronine sodium, dexamethasone sodium phosphate, prednisolone, oxendolone, and leuprorelin acetate.

Examples of the alkaloid drugs include opium, morphine hydrochloride, ipecacuanha, oxycodone hydrochloride, opium alkaloids hydrochlorides, and cocaine hydrochloride.

Examples of the sulfa drugs include sulfisomidin, and sulfamethizole.

Examples of the arthrifuges include allopurinol, and colchicine.

Examples of the antineoplastics include 5-fluorouracil, uracil, and mitomycin.

The content of the active ingredient in the pharmaceutical tablet of the present embodiment is appropriately adjusted according to bioavailability, and is generally 0.01 wt % to 99 wt % in the pharmaceutical tablet. The active ingredient may be diluted with a diluent or the like commonly used in the medical or food fields. In addition, the pharmaceutical tablet of the present embodiment contains one type, or two or more types of active ingredients.

[Other Additives]

The pharmaceutical tablet of the present embodiment may contain various additives as long as the effects of the present invention are not impaired. Examples of such additives include excipients, lubricants, disintegrants, pH adjusters, fluidizers, surfactants, colorants, sweeteners, coating agents, solubilizers, buffers, adsorbents, suspending agents, antioxidants, fillers, dispersants, moisture-proofing agents, and preservatives.

The excipient is a component that is added to make the amount suitable for handling and has no physiological activity. The excipient may be one or two or more excipients selected from, for example, sugar alcohols, sugars, phosphates, crystalline cellulose, starches, silicates, and gelatin. The preferred excipients are sugar alcohols, and sugars.

Examples of the sugar alcohols include mannitol, erythritol, xylitol, sorbitol, and maltitol. Examples of the sugars include white sugar, sucrose, glucose, fructose, lactose, trehalose, maltose, and oligosaccharides. Examples of the phosphates include sodium phosphate and calcium phosphate. Examples of the starches include partially pregelatinized starch and hydroxypropyl starch. Examples of the silicates include sodium silicate, magnesium sodium silicate, and aluminum silicate.

The content of the excipient in the pharmaceutical tablet of the present embodiment is generally 0.01 wt % to 99 wt % in the pharmaceutical tablet.

The lubricant is a component added to improve the fluidity of the powder and facilitate compression formation. Examples of the lubricant include stearic acid, magnesium stearate, calcium stearate, hydrogenated oil, and sodium stearyl fumarate.

The content of the lubricant in the pharmaceutical tablet of the present embodiment is generally 0.01 wt % to 2% wt %, preferably 0.05 wt % to 1.5 wt %, particularly preferably 0.1 wt % to 1% wt % in the pharmaceutical tablet.

The disintegrant is a component added to disintegrate the tablet by absorbing moisture in the body to facilitate the release of the active ingredient. Examples of the disintegrant include carmellose calcium, carboxymethyl starch sodium, croscarmellose sodium, crospovidone, celluloses and derivatives thereof, and starches and derivatives thereof.

Examples of the pH adjuster include citric acid and salts thereof, phosphoric acid and salts thereof, carbonic acid and salts thereof, tartaric acid and salts thereof, fumaric acid and salts thereof, acetic acid and salts thereof, amino acids and salts thereof, succinic acid and salts thereof, and lactic acid and salts thereof.

Examples of the fluidizer include, light anhydrous silicic acid, hydrous silicon dioxide, titanium oxide, stearic acid, a corn gel, and a heavy anhydrous silicic acid.

Examples of the surfactant include phospholipids, glycerin fatty acid esters, polyoxyethylene fatty acid esters, sorbitan fatty acid esters, polyethylene glycol fatty acid esters, polyoxyethylene hydrogenated castor oil, polyoxyethylene alkyl ethers, sucrose fatty acid esters, sodium lauryl sulfate, polysorbates, sodium hydrogen phosphates, and potassium hydrogen phosphates.

Examples of the colorant include iron sesquioxide, yellow iron sesquioxide, food yellow 5, food yellow 4, aluminum chelate, titanium oxide, and talc.

Examples of the sweetener include saccharin, aspartame, acesulfame potassium, thaumatin, and sucralose.

Examples of the coating agent include hydroxypropyl cellulose, hydroxypropyl methylcellulose, methylcellulose, polyvinyl alcohol, polyvinylpyrrolidone-ethyl acrylate, a methyl methacrylate copolymer dispersion, hydroxypropyl methylcellulose acetate succinate, and a methacrylic acid copolymer.

[Pharmaceutical Tablet]

The pharmaceutical tablet of the present embodiment is a pharmaceutical direct tablet obtained by a direct compression method in which the above-described various components are blended and the powder is directly compressed (that is, without performing a granulation step) and molded. It is preferable that the pharmaceutical tablet of the present embodiment is substantially free of water. Accordingly, the tablet hardness can be improved. "Substantially free of water" means that water is not contained as a blending component, and does not exclude even a small amount of water contained in each blending component.

The direct compression method (direct powder compression method) is suitable for in-hospital production because the production process is simple. For molding a pharmaceutical tablet, a tableting machine commonly used in the pharmaceutical field is used. For example, a rotary tableting machine, or a single-shot tableting machine is used.

Generally, in the direct compression method, active ingredients and some additives are uniformly mixed, and then a tableting mixture, to which additives such as a lubricant are added and uniformly mixed, is supplied to a tableting machine such as a rotary tableting machine and compressed and formed, so as to produce the pharmaceutical tablet.

In the present embodiment, the pharmaceutical tablet is obtained by tableting and molding, by a direct compression method, a powder mixture containing an active ingredient and a polyvinyl alcohol resin impregnated with a plasticizer other than water. The PVA resin may be impregnated with the entire amount of plasticizer contained in the pharmaceutical tablet, or the PVA resin may be impregnated with a part of the plasticizer and the remaining amount of the plasticizer may be mixed with the active ingredient.

In a method of impregnating the PVA resin with the plasticizer, when the plasticizer is liquid at 25° C., the entire amount of the liquid plasticizer is charged into a container. A small amount of the PVA resin is added thereto, and the plasticizer and the PVA resin are blended with a spatula or the like. When the mixture is uniform, a small amount of the PVA resin is added again, and the same operation is repeated to produce a PVA resin impregnated with the plasticizer.

When the plasticizer is solid at 25° C., the plasticizer and the PVA resin are mixed in a solid state.

Examples of the tableting machine to be used in tableting-molding include the model "HT-APSS", "HT-AP-MS", "HT-X-SS", and "HT-X-MS" available from Hata Tekkosho Co., Ltd., and "VIRGO", "AQUARIUS", and "LIBRA" available from Kikusui Seisakusho.

The tableting pressure when tableting with the tableting machine is preferably 20 MPa to 300 MPa, and more preferably 50 MPa to 250 MPa. When the tableting pressure is within the above range, practically sufficient moldability and tablet strength can be obtained.

The shape of the pharmaceutical tablet of the present embodiment is not particularly limited, and an ellipsoid, a column, a doughnut, and a sphere can be adopted.

As for the size of the pharmaceutical tablet of the present embodiment, the diameter (longest diameter) is preferably 1 mm to 30 mm, and more preferably 5 mm to 20 mm. The thickness thereof is preferably 1 mm to 10 mm, and more preferably 2 mm to 8 mm.

The pharmaceutical tablet of the present embodiment preferably has a tensile strength of 1.0 MPa or more, particularly 1.1 MPa or more, and more preferably 1.2 MPa or more. When the tensile strength is 1.0 MPa or more, damage is less likely to occur during storage of the pharmaceutical tablet. The upper limit of the tensile strength is generally 10 MPa.

In the present embodiment, the tensile strength of the pharmaceutical tablet is a value calculated using the following equation after measuring the hardness of the pharmaceutical tablet using a hardness meter (load cell type tablet hardness meter PC-30 type, manufactured by Okada Seiko Co., Ltd.).

$$T.S. = 2P/(\pi \times D \times T)$$

T. S.: tensile strength (MPa) of tablet
P: hardness (N) of tablet
D: diameter (mm) of tablet
T: thickness (mm) of tablet Examples of the method of adjusting the tensile strength of the pharmaceutical tablet to the above range include a method of containing the plasticizer in the pharmaceutical tablet and a method of appropriately changing the tableting pressure of the tableting machine.

The disintegration time of the pharmaceutical tablet of the present embodiment is preferably 60 seconds or shorter, more preferably 1 to 50 seconds, and particularly preferably 3 to 30 seconds as measured according to a pharmacopoeia disintegration test in the 17th edition of Japanese Pharmacopoeia. When the disintegration time is within the above range, the dissolution control during administration of the pharmaceutical tablet is easy.

Examples of the method of adjusting the disintegration time of the pharmaceutical tablet to the above range include a method of changing the tableting pressure of the tableting machine appropriately or adding a disintegrant.

The water content of the pharmaceutical tablet of the present embodiment is preferably 3 wt % or less, and more preferably 0.01 wt % to 1 wt %. The water content can be measured by a loss on drying measurement method. As described above, the water content can be controlled within the above range by not containing water substantially as a blending component.

EXAMPLES

Hereinafter, although the present invention is demonstrated further more concretely by ways of Examples, the present invention is not limited to following Examples, unless the gist of the present invention is exceeded.

"Part" in Examples and Comparative Examples is based on weight.

In the following Examples and Comparative Examples, the average degree of polymerization and the degree of saponification of the PVA resin were measured according to JIS K6726, and the average particle size was determined as a 50% particle size which is the diameter at 50% in the cumulative value (cumulative distribution) obtained from the measured laser diffraction volume distribution by particle size.

Example 1

The tablet was prepared by the following method.

100 parts of a PVA resin (average degree of polymerization 2600, degree of saponification 88 mol %, content of alkali metal salt 0.03 wt %, and average particle size 58 μm) and 3.1 parts of glycerin were mixed to prepare a PVA resin impregnated with glycerin. Crystalline mannitol (manufactured by Mitsubishi Corporation Life Sciences Limited, "Mannit P") and magnesium stearate were prepared. To the above PVA resin impregnated with glycerin, 923 parts of the crystalline mannitol and 5.2 parts of magnesium stearate were added and mixed for 3 hours to prepare a uniform powder mixture.

0.2 g of the prepared powder mixture was weighed, charged into a flat mold having a diameter of 8 mm, and pressed using a tableting machine ("TAB ALL" manufactured by Okada Seiko Co., Ltd.) at 200 MPa to obtain a tablet.

The obtained tablet was measured for tensile strength and disintegration time.

<Measurement of Tensile Strength>

The tensile strength was calculated using the following equation after measuring the hardness of the tablet using a hardness meter (load cell type tablet hardness meter PC-30 type, manufactured by Okada Seiko Co., Ltd.).

$$T.S. = 2P/(\pi \times D \times T)$$

T. S.: tensile strength (MPa) of tablet
P: hardness (N) of tablet
D: diameter (mm) of tablet
T: thickness (mm) of tablet <Measurement of Disintegration Time>

The disintegration time of the tablet obtained as above was measured using a pharmacopoeia disintegration test in the 17th edition of Japanese Pharmacopoeia.

Equipment: Disintegration tester NT-200 type (manufactured by Toyama Sangyo Co., Ltd.)
Solution: 1000 mL distilled water
Solution temperature: 37° C.

Example 2

A tablet was prepared in the same manner as in Example 1 except that the component in Example 1 was changed as shown in Table 1, and the tensile strength and the disintegration time were measured.

Comparative Example 1

A tablet was prepared in the same manner as in Example 1 except that the component in Example 1 was changed as shown in Table 1, and the tensile strength and the disintegration time were measured.

Comparative Example 2

A tablet was prepared in the same manner as in Example 1 except that the component in Example 1 was changed as shown in Table 1, and the tensile strength and the disintegration time were measured.

TABLE 1

| | Content (part by weight) | | | | Evaluation | |
|---|---|---|---|---|---|---|
| | PVA resin | Glycerin | Mannitol | Magnesium stearate | Tensile strength (MPa) | Disintegration time (second) |
| Example 1 | 100 | 3.1 | 923 | 5.2 | 1.43 | 26.7 |
| Example 2 | 100 | 5.3 | 942 | 5.3 | 1.22 | 28.0 |
| Comparative Example 1 | 100 | 0 | 895 | 5.0 | 0.66 | 171.0 |
| Comparative Example 2 | 100 | 11.1 | 994 | 5.6 | 0.21 | 55.0 |

It is seen from the results of Examples 1 and 2 in Table 1 that when using a PVA resin impregnated with a plasticizer (glycerin), the tensile strength is higher and the immediate disintegrability is superior compared to Comparative Example 1 without blending a plasticizer (glycerin).

Further, Comparative Example 2 containing 11.1 parts of a plasticizer (glycerin) has a low tensile strength and takes time to disintegrate.

In the above Examples and Comparative Examples, a model experiment is conducted on a tablet without blending an active ingredient. However, it is presumed that the same tensile strength and disintegration time as in the above Examples and Comparative Examples can be obtained also in a pharmaceutical tablet containing a pharmaceutical tablet.

Although the present invention has been described in detail with reference to specific embodiments, it will be apparent to those skilled in the art that various changes and modifications can be made without departing from the spirit and scope of the present invention. The present application is based on a Japanese Patent Application (2017-153172) filed on Aug. 8, 2017, contents of which are incorporated herein by reference.

INDUSTRIAL APPLICABILITY

Since the pharmaceutical tablet of the present invention has high tensile strength and excellent in immediate disintegrability, it can be suitably used as a tablet for oral administration of pharmaceuticals or quasi-drugs, particularly as a rapidly disintegrating tablet in the oral cavity.

The invention claimed is:

1. A pharmaceutical tablet obtained by a direct compression method, the pharmaceutical tablet comprising:
    an active ingredient;
    a polyvinyl alcohol resin having a degree of saponification of 70 mol % to 100 mol %, wherein the polyvinyl alcohol resin is an unmodified polyvinyl alcohol consisting of vinyl alcohol structural units and polyvinyl ester structural units; and
    a plasticizer other than water in an amount of 1 to 8 parts by weight with respect to 100 parts by weight of the polyvinyl alcohol resin,
    wherein the plasticizer is a liquid polyhydric alcohol at 25° C.

2. The pharmaceutical tablet according to claim 1, wherein the polyvinyl alcohol resin has an average degree of polymerization of 2100 to 4000.

3. The pharmaceutical tablet according to claim 1, having a tensile strength of 1.0 MPa or more.

4. The pharmaceutical tablet according to claim 1, which is substantially free of water.

5. A method for producing a pharmaceutical tablet, the method comprising: tableting and molding, by a direct compression method, a powder mixture containing an active ingredient and a polyvinyl alcohol resin impregnated with a plasticizer other than water in an amount of 1 to 8 parts by weight with respect to 100 parts by weight of the polyvinyl alcohol, wherein the polyvinyl alcohol resin has a degree of saponification of 70 mol % to 100 mol %, and the polyvinyl alcohol resin is an unmodified polyvinyl alcohol consisting of vinyl alcohol structural units and polyvinyl ester structural units, wherein the plasticizer is a liquid polyhydric alcohol at 25° C.

\* \* \* \* \*